(12) United States Patent  
McClellan

(10) Patent No.: US 10,265,133 B1  
(45) Date of Patent: Apr. 23, 2019

(54) STERILE DRAPE HAVING TRANSPARENT POCKET

(71) Applicant: Aaron McClellan, Lebanon, NH (US)

(72) Inventor: Aaron McClellan, Lebanon, NH (US)

( * ) Notice: Subject to any disclaimer, the term of this patent is extended or adjusted under 35 U.S.C. 154(b) by 0 days.

(21) Appl. No.: 15/928,480

(22) Filed: Mar. 22, 2018

(51) Int. Cl.
| | | |
|---|---|---|
| *A61B 19/08* | (2006.01) | |
| *A61B 46/23* | (2016.01) | |
| *A61B 46/00* | (2016.01) | |
| *A61B 46/20* | (2016.01) | |

(52) U.S. Cl.
CPC .............. *A61B 46/23* (2016.02); *A61B 46/40* (2016.02); *A61B 2046/205* (2016.02); *A61B 2046/236* (2016.02)

(58) Field of Classification Search
CPC ... A61B 46/00; A61B 46/20; A61B 2046/201; A61B 2046/205; A61B 46/23; A61B 2046/234; A61B 2046/236; A61B 46/40; A61B 46/30
See application file for complete search history.

(56) References Cited

U.S. PATENT DOCUMENTS

| | | | |
|---|---|---|---|
| 3,800,790 A * | 4/1974 | Collins | A61B 46/00 128/854 |
| 4,323,062 A | 4/1982 | Canty | |
| 4,476,860 A | 10/1984 | Collins et al. | |
| 4,905,710 A * | 3/1990 | Jones | A61B 46/00 128/849 |
| 4,957,120 A | 9/1990 | Grier-Idris | |
| 5,335,677 A | 8/1994 | Busch | |
| 5,339,831 A | 8/1994 | Thompson | |
| 5,605,546 A | 2/1997 | Wolzinger et al. | |
| 5,988,172 A | 11/1999 | Sosebee | |
| 6,615,836 B1 | 9/2003 | Griesbach et al. | |
| 7,343,919 B2 | 3/2008 | Czajka et al. | |
| 8,807,138 B2 | 8/2014 | Byers et al. | |
| 2012/0008880 A1 | 1/2012 | Toth | |
| 2014/0318551 A1 | 10/2014 | Daly | |
| 2015/0101616 A1 | 4/2015 | Wiley et al. | |
| 2015/0305816 A1 * | 10/2015 | Hadzic | A61N 1/0502 128/852 |
| 2016/0008073 A1 * | 1/2016 | Pecora | A61B 46/23 128/852 |

FOREIGN PATENT DOCUMENTS

| | | |
|---|---|---|
| DE | 102015101207 A1 | 7/2016 |
| WO | 2016061241 A1 | 4/2016 |

\* cited by examiner

*Primary Examiner* — Victoria J Hicks  
(74) *Attorney, Agent, or Firm* — Ryan C. Stockett

(57) ABSTRACT

A drape is disclosed for use during a surgical procedure in a sterile work area. The drape may include a cloth configured to at least partially cover a patient during a surgical procedure. The cloth may have a patient-side and a physician-side. The drape may also include a pocket attached to the cloth. The pocket may have at least one wall that is at least partially transparent, and an opening that is accessible via only the patient-side of the cloth.

18 Claims, 2 Drawing Sheets

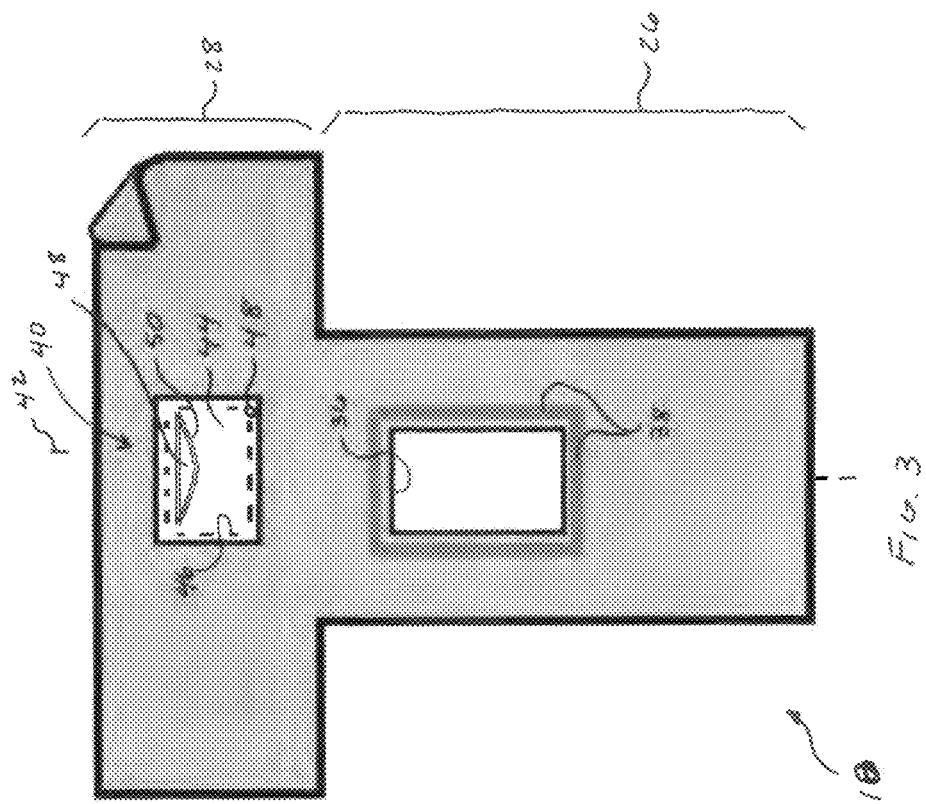
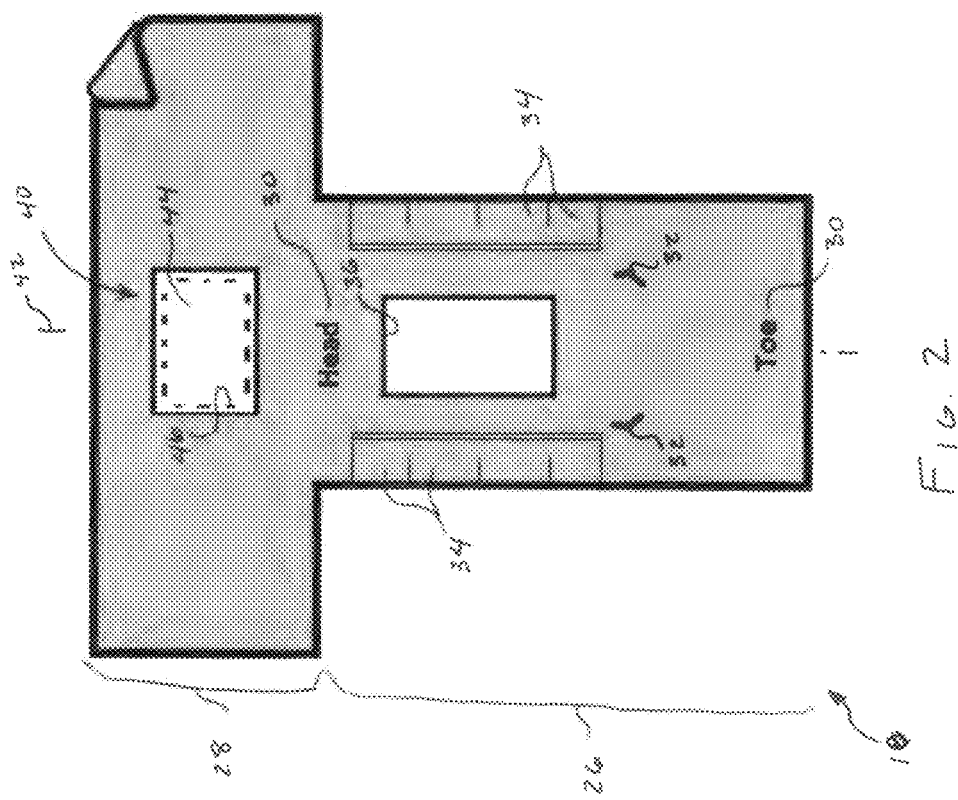

US 10,265,133 B1

STERILE DRAPE HAVING TRANSPARENT POCKET

TECHNICAL FIELD

The present disclosure relates generally to a drape and, more particularly, to a sterile drape having a transparent pocket.

BACKGROUND

Draping is the placement of drapes on and around a patient, after the skin of the patient has been prepared for surgery. The purpose of draping is to provide a sterile work area around a surgical site. Drapes function as impervious barriers between non-sterile surfaces and the sterile work area. They allow a team of scrubbed practitioners to work freely, without risking contamination of the surgical site. Once the patient is draped, sterile equipment is thereafter moved into position, close to the surgical patient.

Often during surgery, changes to the environment and/or information may be needed. For example, adjustments to lighting, room temperature, music, patient positioning, cautery adjustments, tourniquet adjustments, etc. may be requested by one of the scrubbed practitioners (e.g., by the surgeon). In another example, images (e.g., x-rays, photos, diagrams, etc.), procedural data, drug-related facts, and other information may be helpful. Traditionally, one of the scrubbed practitioners (e.g., a nurse or anesthetist) will respond to the surgeon's requests (e.g., by leaving the sterile work area to make the required adjustments and/or to look up the required information at a remote station). Doing so, however, risks contamination of the scrubbed practitioner and/or takes a focus of the practitioner away from the patient. In other instances, an electronic device (e.g., a laptop or notebook computer) may be sterilized and brought into the surgical area for use in making the adjustments and/or displaying the required information. Sterilizing such a device for entry into the surgical area, however, can be a complex and resource-intensive activity.

The drape of the present disclosure solves one or more of the problems set forth above and/or other problems in the art.

SUMMARY

In one aspect, the present disclosure is directed to a surgical drape. The surgical drape may include a cloth configured to at least partially cover a patient during a surgical procedure. The cloth may have a patient-side and a physician-side. The surgical drape may also include a pocket attached to the cloth. The pocket may have at least one wall that is at least partially transparent, and an opening that is accessible via only the patient-side of the cloth.

In another aspect, the present disclosure is directed to another surgical drape. This surgical drape may include an impermeable cloth having a first side and a second side. The surgical drape may also include an adhesive surface located at only the second side, and a transparent pocket attached to the cloth. An opening into the pocket may be accessible via only the second-side of the impermeable cloth.

In yet another aspect, the present disclosure is directed to another surgical drape. This surgical drape may include an at least partially transparent cloth having a patient-side and a physician-side, and an attachment device connectable to the at least partially transparent cloth, the attachment device configured to hold a non-sterile object for observation through the at least partially transparent cloth from the physician-side.

BRIEF DESCRIPTION OF THE DRAWING

FIG. 1 is a perspective illustration of an exemplary disclosed surgical theater; and FIGS. 2 and 3 are front and back plan-view illustrations of an exemplary drape that may be utilized in conjunction with the surgical theater of FIG. 1.

DETAILED DESCRIPTION

FIG. 1 illustrates an exemplary surgical theater 10, in which one or more medical practitioners (e.g., anesthetists, nurses, surgeons, etc.) 12 may perform surgery on a patient 14. In the disclosed embodiment, the patient 14 is recumbent on a support surface (e.g., an operating platform or bed) 16. It is contemplated, however, that the patient 14 may be positioned in any manner and on any type of support surface 16 known in the art.

As shown in FIG. 1, the patient 14 may be prepared for surgery via draping. As described above, draping involves the application of one or more drapes 18 on and/or around the patient 14, after the skin of the patient has been prepared at an intended site of the surgery. Draping is a well-known multi-step process for creating a sterile work area.

Drape 18 may be configured to hold a non-sterile object 20 in a manner that allows display of object 20 within the sterile work area, without risking contamination of the sterile work area. In the disclosed embodiment, object 20 is an electronic device (e.g., a laptop computer, a notebook computer, a smart phone, a tablet, etc.). It is contemplated, however, that object 20 could be a non-electronic device (e.g., an x-ray film, a photo, a chart, etc.), if desired.

In the embodiment depicted in FIG. 1, drape 18 includes a first or horizontal-portion 22 and a second or upright-portion 24. Horizontal-portion 22 of drape 18 may be placed over the prone patient 14, while upright-portion 24 may be located at an end of horizontal-portion 22 and held upright by a separate frame 25. In some embodiments, upright-portion 24 is located at a neck area of the patient 14, such that the head of the patient 14 extends out past upright-portion 24. Horizontal-portion 22 may extend from the neck area of the patient past a foot area. It should be noted, however, that drape 18 may be positioned and/or used in another manner, if desired. As will be described in more detail below, object 20 may generally be located within upright-portion 24. It is contemplated, however, that object 20 (or another sterile or non-sterile object—not shown) could additionally or alternatively be held within horizontal-portion 22. It is also contemplated that drape 18 could include only horizontal-portion(s) 22 or only upright-portion(s) 24.

Horizontal- and/or upright-portions 22, 24 may be fabricated from a flexible cloth (e.g., a panel of a natural material such as cotton, silk, wool, etc.; a synthetic material such as nylon, polyester, acrylic, etc.; a hybrid material such as synthetic fiber-reinforced, coated, and/or blended natural material; or a plastic sheet). In some instances, the flexible cloth is moisture impermeable. In exemplary embodiments, horizontal- and upright-portions 22, 24 are integral portions of the same cloth. In other embodiments, however, horizontal-portion 22 may initially be separate from upright-portion 24 and thereafter temporarily or permanently joined together (e.g., via stitching, Velcro, ties, zippers, etc.).

Opposing sides of drape 18 are shown in FIGS. 2 and 3. FIG. 2 illustrates a physician-side of drape 18 (e.g., a side that is oriented toward the sterile work area), while FIG. 3 illustrates a patient-side of drape 18 (e.g., a side that is oriented toward the patient and/or away from the sterile work area). As can be seen in both of these figures, drape 18 may be generally T-shaped, having a stem-portion 26 and a cross-portion 28. In general, upright-portion 24 may correspond with cross-portion 28, while horizontal-portion 22 may correspond with stem-portion 26. Accordingly, object 20 (referring to FIG. 1) may generally be located within cross-portion 28. It is contemplated, however, that drape 18 could have another shape (e.g., a completely rectangular shape) and/or that object 20 could additionally or alternatively be located within stem-portion 26, if desired.

The physician-side of drape 18 be identified in any number of different ways. For example, the physician-side of drape 18 may include markings (e.g., head-markings, toe markings, side-markings, top/bottom markings, "physician" markings, etc.) 30 indicating an intended orientation of drape 18 on the patient 14. In another example, one or more instrument securing devices (e.g., tie, straps, Velcro, clips, etc.) 32 may be provided at the physician-side of drape 18 for use in securing equipment (e.g., hoses, cords, etc.) during surgery. In yet another example, one or more collection pouches 34 may be affixed to drape 18 at opposing sides of a fenestration 36. Pouches 34 may be open at an edge facing fenestration 36, such that fluids discharging from the patient's wound may be collected therein. Other ways (e.g., colors, surface texture, etc.) of identifying the physician-side of drape 18 may also be available.

The patient-side of drape 18 also be identified in any number of different ways. For example, the patient-side of drape 18 may include adhesive strips 38 that function to hold drape 18 in a secure position relative to the patient. In one embodiment, adhesive strips 38 are located around fenestration 36. In other embodiments, adhesive strips 38 are in other locations (at edges of drape 18). It is also contemplated that an entire surface at the patient-side of drape 18 could be provided with a tacky texture that inhibits undesired movements of drape 18. Other ways (e.g., colors, markings, etc.) of identifying the patient-side of drape 18 may also be available.

Object 20 (referring to FIG. 1) may be held by drape 18 (e.g., by the upright- and cross-portions 24, 28) via a pocket 40 formed within drape 18. Pocket 40 may have any desired shape and size. In the disclosed embodiment, pocket 40 is generally rectangular and sized to receive therein a tablet-type of object 20 (e.g., an iPad) such that a screen of object 20 can be interfaced with by a scrubbed medical practitioner during the surgical procedure. For example, pocket 40 may have a first dimension that is about 6-10 inches, and a transverse dimension that is about 8-12 inches. It is contemplated, however, that pocket 40 could be round, ellipsoid, triangular, or have any other shape known in the art. It is also contemplated that pocket 40 could be smaller to accommodate a personal electronic (e.g., a smart phone), or larger to accommodate a computer (e.g., a laptop or notebook). Pocket 40 may generally be aligned with a line of symmetry 42 of drape 18 that passes through a center of fenestration 36. However, other alignments are also contemplated.

Pocket 40 may have any number of walls required to form a generally enclosed space in which object 20 may reside. In one embodiment, pocket 40 includes a single wall 44 that is affixed to the physician-side of the cloth making up drape 18, such that object 20 is held between the cloth and wall 44. In another embodiment, pocket 40 includes opposing walls 44 that are affixed to opposing sides of drape 18 (e.g., at an opening 46), such that object 20 is held between walls 44. Wall(s) 44 may be affixed to the cloth of drape 18 and/or to each other in multiple different ways. For example, wall(s) 44 may be chemically affixed (e.g., via an adhesive), mechanically affixed (e.g., via stitching, Velcro, staples, buttons, rivets, etc.), and/or thermally affixed (e.g., via melting of at least a portion of the cloth and/or wall(s) 44). In one embodiment, pocket 40 is completely formed and thereafter affixed to the cloth of drape 18. In other embodiments, however, pocket 40 is formed by the affixing. It should be noted that pocket 40 may have more than two walls (e.g., perimeter walls—not shown) 44, if desired, to accommodate thicker objects 20.

At least one wall 44 of pocket 40 may be at least partially transparent. For example, at least the wall 44 exposed at the physician-side of drape 18 may be transparent, such that object 20 maybe at least partially visible in the sterile work area during surgery by a scrubbed medical practitioner via wall 44. It is contemplated, however, that both opposing walls 44 may be at least partially transparent, if desired. Pocket 40 may be impermeable and/or hermetically sealed.

Pocket 40 may include one or more openings 48 located at only the patient-side of drape 18. Opening(s) 48 may have any size, shape, and/or orientation, and may be formed within the cloth of drape 18 and/or within wall 44 at the patient-side. Opening(s) 48 may provide access to pocket 40 for the insertion, manipulation, and/or retrieval of object 20. It is also contemplated that opening(s) 48 may provide access for charging and/or remote communication with object 20 (e.g., a charging or communication cord hole).

In some embodiments, a closing device 50 is associated with opening 48. Closing device 50 may include, for example, buttons, snaps, a zipper, an adhesive, etc.

INDUSTRIAL APPLICABILITY

The disclosed drape may be used for any type of medical procedure, where improved access to environmental controls and/or information may be helpful. The disclosed drape may provide a way to support a non-sterile object (e.g., an electronic device) for access from the sterile work area, without risk of contamination. Use of drape 18 will now be described in detail, with reference to FIGS. 1-3.

In preparation for a medical procedure, after a patient 14 has been prepped, drape 18 may be carefully placed over the patient 14 and over frame 25 following standard protocol. Thereafter, object 20 may be placed inside pocket 40 from the patient-side of drape 18 via opening 48. For the purposes of this disclosure, drape 18, object 20, and frame 25 may together be considered a drape assembly 52. Because object 20 can be placed into pocket 40 from only the patient-side of drape 18, and is not directly accessible from the physician-side, object 20 may not need to be sterilized. In addition, the display screen of object 20 may be visible via transparent wall 44, and functionality of object 20 may be accessed by a user that is scrubbed into the sterile work area. For example, the user may be able to push buttons (virtual and/or real buttons) to adjust music, lighting, patient position, temperature, cautery adjustment, tourniquet adjustment, etc. In addition, the user may be able to pull up images, anesthesia information, procedural instructions, diagrams, patient record, web-access, remote communications access (e.g., live visual and/or audio meetings), vital signs, and other information.

The disclosed drape may provide many benefits. For example, scrubbed medical practitioners may have direct access to environmental controls and/or information without having to leave the sterile work area or to rely on others for the desired adjustments and/or information. In addition, other practitioners normally tasked with making the indirect adjustments and/or retrieving information for the practitioners in the sterile work area may be better able to focus on their primary tasks. Furthermore, functionality heretofore not available within the sterile work area may now be accessible, allowing for a higher level of care.

It will be apparent to those skilled in the art that various modifications and variations can be made to the disclosed drape without departing from the scope of the disclosure. Other embodiments of the drape will be apparent to those skilled in the art from consideration of the specification and practice of the system disclosed herein. It is intended that the specification and examples be considered as exemplary only, with a true scope of the disclosure being indicated by the following claims and their equivalents.

What is claimed is:

1. A surgical drape, comprising:
   a cloth configured to at least partially cover a patient during a surgical procedure, the cloth having a patient-side and a physician-side and a general T-shape, including a single layer stem-portion and a single layer cross-portion;
   a pocket attached to the cloth and located within the single layer cross-portion, wherein the pocket has:
      at least one wall that is at least partially transparent; and
      an opening that is accessible via only the patient-side of the cloth; and
   a fenestration formed in the single layer stem-portion of the cloth, wherein the pocket is generally aligned with the fenestration along a line of symmetry of the cloth.

2. The surgical drape of claim 1, wherein the pocket is formed by only a single wall attached to the cloth.

3. The surgical drape of claim 2, wherein the single wall is flat.

4. The surgical drape of claim 3, wherein the single wall is rectangular.

5. The surgical drape of claim 4, wherein the single wall is sealed to the cloth on at least three edges.

6. The surgical drape of claim 4, wherein the single wall is sealed to the cloth on all edges.

7. The surgical drape of claim 1, wherein the pocket is formed by only two opposing walls attached to the cloth.

8. The surgical drape of claim 7, wherein the two opposing walls are flat.

9. The surgical drape of claim 1, wherein the pocket is configured to receive at least one of a laptop computer, a notebook computer, and a tablet.

10. The surgical drape of claim 9, wherein the pocket has a rectangular shape with a first dimension of 6-10 inches and a transverse dimension of 8-12 inches.

11. The surgical drape of claim 1, further including at least one of the following located at the physician-side of the cloth:
    an intended orientation marking;
    a collection pouch configured to collect fluids discharging from a wound of the patient; and
    an instrument securement device.

12. The surgical drape of claim 1, further including an adhesive surface located at the patient-side of the cloth.

13. The surgical drape of claim 1, further including a closure mechanism associated with the opening.

14. The surgical drape of claim 1, wherein the pocket further includes a cord hole that is accessible from only the patient side of the cloth.

15. The surgical drape of claim 1, wherein:
    the cloth has a first portion configured to cover a patient from a neck area past a foot area, and a second portion located at an end of the first portion;
    the second portion is configured to separate a head end of the patient from the physician-side of the cloth at the first-portion, without covering a head of the patient; and
    the pocket is located in the second-portion of the cloth.

16. The surgical drape of claim 1, wherein the cloth is impermeable.

17. The surgical drape of claim 1, wherein the at least one wall of the pocket is impermeable.

18. The surgical drape of claim 1, wherein the pocket is formed by a flat end wall, and a perimeter wall that is attached between the cloth and the flat end wall.

* * * * *